US006565961B2

(12) United States Patent
Koslow

(10) Patent No.: US 6,565,961 B2
(45) Date of Patent: *May 20, 2003

(54) ABSORBENT ARTICLES

(75) Inventor: Evan Koslow, Weston, CT (US)

(73) Assignee: Koslow Technologies Corporation ( * ) Notice: Subject to any disclaimer, the term of this patent is extended or adjusted under 35 U.S.C. 154(b) by 0 days.

This patent is subject to a terminal disclaimer.

(21) Appl. No.: 10/096,355

(22) Filed: Mar. 11, 2002

(65) Prior Publication Data

US 2002/0187302 A1 Dec. 12, 2002

Related U.S. Application Data

(60) Continuation-in-part of application No. 09/358,183, filed on Jul. 20, 1999, now Pat. No. 6,355,330, which is a continuation-in-part of application No. 08/903,395, filed on Jul. 22, 1997, now Pat. No. 6,077,588, which is a division of application No. 08/813,055, filed on Mar. 7, 1997, now Pat. No. 5,792,513.

(51) Int. Cl.[7] .............................................. A61F 13/15
(52) U.S. Cl. ................... 428/304.4; 604/380; 604/382; 428/308.4
(58) Field of Search ........................ 428/304.4, 308.4; 604/382, 380

(56) References Cited

U.S. PATENT DOCUMENTS

| 4,759,782 | A | * | 7/1988 | Miller et al. .................. 55/487 |
| 5,411,497 | A | * | 5/1995 | Tanzer et al. ................ 604/368 |
| 5,562,645 | A | * | 10/1996 | Tanzer et al. ................ 604/367 |
| 5,573,994 | A | | 11/1996 | Kabra et al. |
| 5,587,107 | A | | 12/1996 | Schwertfeger et al. |
| 5,605,937 | A | | 2/1997 | Knaus |
| 5,676,660 | A | * | 10/1997 | Mukaida et al. ............. 604/375 |
| 5,750,585 | A | | 5/1998 | Park et al. |
| 5,925,299 | A | | 7/1999 | Dierckes, Jr. et al. |
| 5,998,493 | A | | 12/1999 | Mitchell et al. |
| 6,015,608 | A | * | 1/2000 | Koslow .................... 428/304.4 |
| 6,232,520 | B1 | * | 5/2001 | Hird et al. .................. 604/368 |
| 6,245,051 | B1 | * | 6/2001 | Zenker et al. .......... 604/385.23 |

* cited by examiner

*Primary Examiner*—Cathy Lam
(74) *Attorney, Agent, or Firm*—Shirley Ma

(57) ABSTRACT

An absorbent article containing a composite mixture of absorbent macroporous particles and binder particles. Preferably, the absorbent macroporous particles are those having a macroporous structure which allow for the rapid flow of liquid therein, e.g., aerogels, xerogels, cryogels, or mixtures thereof. The absorbent articles produced thereby are preferably thin and lightweight, but maintain an ample rate of absorption allowing for a more rapid uptake of higher volumes of liquids.

14 Claims, 2 Drawing Sheets

ABSORBENT ARTICLES

RELATED APPLICATIONS

This application is a continuation-in-part of co-pending U.S. patent application Ser. No. 09/358,183, filed Jul. 20, 1999 now U.S. Pat. No. 6,355,330, which is a continuation-in-part of U.S. patent application Ser. No. 08/903,395, filed Jul. 22, 1997, that issued as U.S. Pat. No. 6,077,588, which is a division of U.S. patent application Ser. No. 08/813,055, filed Mar. 7, 1997, that issued as U.S. Pat. No. 5,792,513.

BACKGROUND OF THE INVENTION

I. Field of the Invention

The present invention relates generally to absorbent articles. Particularly, the present invention relates to absorbent articles containing macroporous absorbent materials that provide quick absorption and subsequent containment of liquid. More particularly, the present invention relates to absorbent articles containing aerogels.

II. Description of the Prior Art

It is often desirable to impregnate, cover, or otherwise treat a base material with an absorbent or adsorbent material to form an absorbent article. Examples are found in children's diapers, adult incontinence products, and feminine hygiene products. Other examples include coated paper tissues, toweling, and surgical bandages.

The active adsorbent or absorbent materials used to coat a base material may be fibrous, particulate or both. Fluff pulp is a fibrous absorbent well known in the art. However, fluff pulp fibers have limited absorption capacity and as such, do not always meet the expectations of normal use. In addition, fluff pulp fibers are heavy and bulky, and impart these characteristics into products that contain fluff pulp fibers.

Super adsorbent polymers (hereinafter SAP) in powdered or granular form provide enhanced absorptive capacity over traditional fluff pulp when used alone, or when used in combination with fluff pulp fiber. However, SAP particles that are not well dispersed within an absorbent product undergo a phenomenon known as "gelling" or "gel blocking".

Contact of SAP with liquid causes SAP to swell. Upon contact with liquid, SAP polymer particles in close proximity coalesce to create an SAP gel of limited permeability. Once formed, the SAP gel prevents utilization of underlying absorbent by blocking access thereto.

The effect of SAP gelling on absorption is of particular concern when the absorbent is used in combination with fluff pulp fibers. This problem is made worse by the well-known and often practiced method of bonding a high percentage of SAP particles directly to the fibers contained in the absorbent article.

In light of the foregoing, there exists a need for improved absorbent articles that are thin, light weight and effective. Still further, there exists a need for adsorbent and absorbent articles free of fluff pulp fibers, having both internal porosity suitable for bulk absorption and subsequent containment of liquid.

SUMMARY OF THE INVENTION

The present invention describes an absorbent article comprising a first substrate and a laminate, wherein the laminate comprises a mixture of binder particles and absorbent macroporous particles.

In addition, the present invention includes the above absorbent article, wherein the binder particles are on average smaller than the absorbent macroporous particles.

Furthermore, the present invention includes the above absorbent article, wherein at least some of the absorbent macroporous particles are coalesced by the binder particles to each other, to the first substrate, or to both each other and to the first substrate.

The present invention also includes the above absorbent article further comprising a second substrate on the laminate, optionally wherein at least some of the absorbent macroporous particles are coalesced or fused by the binder particles to the second substrate, and said laminate is in-between the first substrate and the second substrate.

The present invention also describes an absorbent article, wherein the absorbent macroporous particles are produced by a process comprising the steps of forming a liquid-containing gel, and then removing the liquid from the gel in a way sufficient to produce absorbent macroporous particles.

This invention will be discussed in greater detail in the description that follows. Additional advantages of the invention will become apparent from this discussion, together with accompanying drawings.

DETAILED DESCRIPTION OF THE INVENTION

Figure 1:
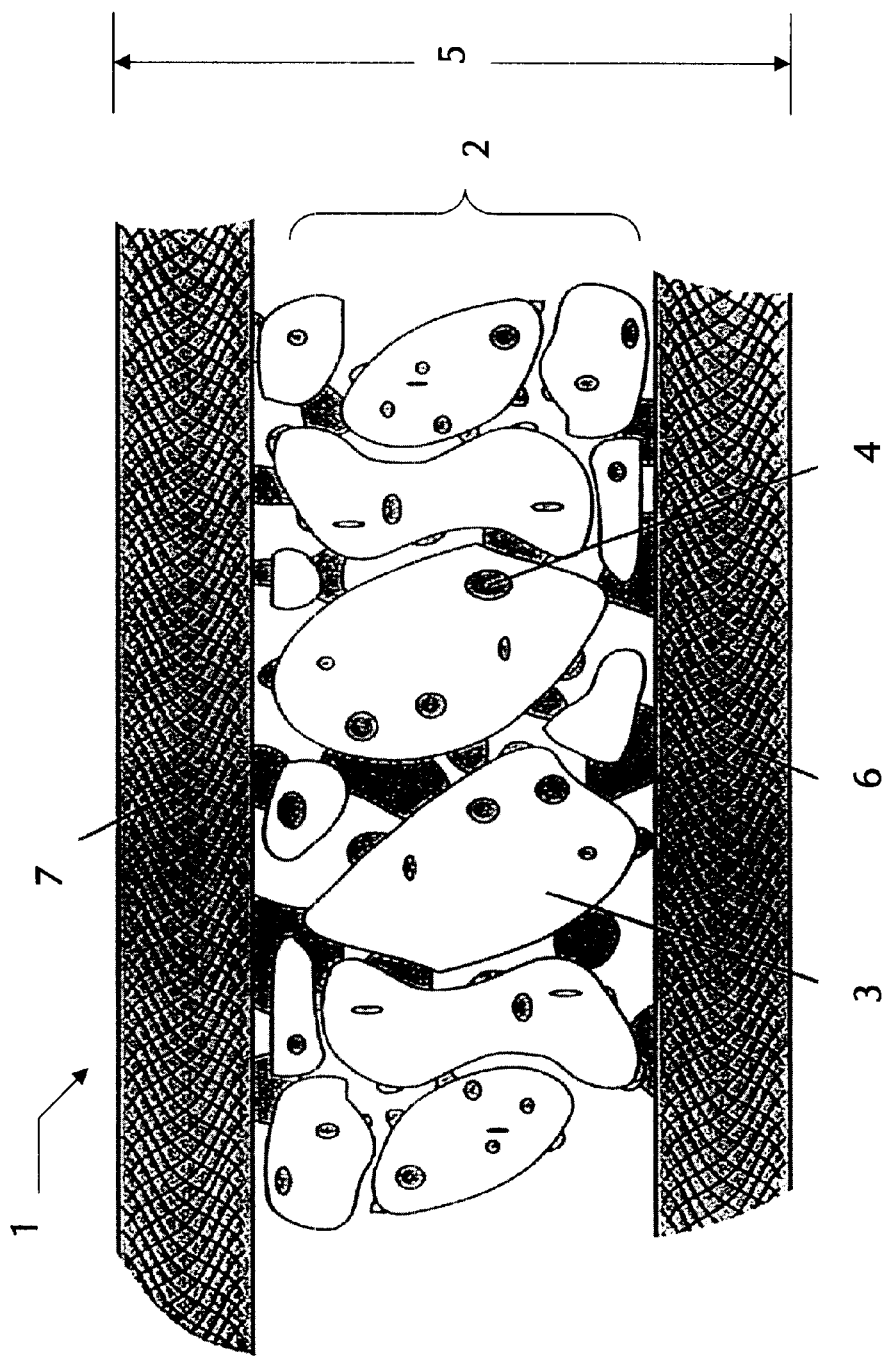
FIG. 1 is a side plan-view of the adsorbent media of the present invention.

Referring to the drawings and, in particular, FIG. 1, there is provided an absorbent article generally indicated as 1. Related absorbent articles and the methods for producing them are also described in U.S. Pat. Nos. 6,077,588 and 5,792,513, which are incorporated herein by reference.

Absorbent article 1 has a first substrate 6 and optionally a second substrate sometimes referred to as a covering layer or top sheet 7. First substrate 6 and second substrate 7 may be formed of various materials depending upon the intended application, and need not be formed of the same or similar material within one composite. By way of example only, substrates 6 and/or 7 may be permeable materials such as non-woven fibrous webs, e.g., spun bonded, melt blown or carded materials composed of polyester or polyolefinic fibers. The substrates may also be formed from woven materials. Substrates 6 and/or 7 may optionally be formed wholly or in part from cellulosic materials including tissue or towel stock. In the alternative, substrates 6 and/or 7 may be semi-permeable to liquids, e.g., a membrane, or a porous polymeric film, or can be impermeable to liquids, such as, for example, a plastic film.

The particular material selected for first substrate 6 and/or second substrate 7 can effect the kinetics of absorption of absorbent article 1. For example, first substrate 6 and/or second substrate 7 can modify the mean pore size, the overall porosity, and permeability of the absorbent article. They can also provide supplemental absorption, improve tensile strength, flexibility, pleatability, effect wicking and effect fluid distribution within absorbent article 1.

Coalesced with first substrate 6, and optionally with second substrate 7, is a laminate indicated generally as 2. Laminate 2 is comprised of absorbent macroporous particles 3 and binder particles 4. The binder particles 4 coalesce at least some of the absorbent macroporous particles 3. An amount of binder particles 4 also coalesce at least some of the absorbent macroporous particles 3 to substrate 6, and optionally to substrate 7, or to both substrates 6 and 7.

The size distribution of the absorbent macroporous particles 3 is typically from about 5 microns to about 5000 microns, preferably from about 140 microns to about 865 microns.

Any suitable binder material may be employed in this invention. Materials suitable for forming binder particles 4 include, but are not limited to: thermoplastic and/or thermosetting binders. Preferred binder materials are hydrophobic, and include, polyethylene, polypropylene, poly (ethylene vinyl acetate), and nylon.

Binder particles 4 are on average smaller than the absorbent macroporous particles 3, generally having a size from about 0.1 microns to about 100 microns. Preferably, binder particles 4 are 4 to 25 times smaller in size, on average, than absorbent macroporous particles 3.

Thickness 5 of composite 1 will vary depending on a variety of factors including, the size of absorbent macroporous particles 3, binder particles 4, and the quantity of particles 3 and 4 per unit area. Thickness 5 of composite 1 is generally about 0.2 mm to about 10 mm, preferably from about 1 mm to about 2 mm.

Absorbent macroporous particles 3 have large pores that provide rapid wicking, quick absorption of liquids, and can hold a large amount of fluid within in the absence of traditional absorbent materials such as, for example, fluff pulp. As used herein, the terms macropore or macroporous particle refer to particles having pores of a size from about 90 nanometers to about 1,000 nanometers across.

Absorbent macroporous particles 3 can be produced in several ways. For example, polyethylene beads containing a chemical crosslinking agent, such as dicumyl peroxide, can be suspended in an aqueous solution and heated to a suitable temperature to trigger a crosslinking reaction. The resultant crosslinked resin is then impregnated with a hydrocarbon or chlorofluorocarbon blowing agent, such as butane. Drying the resin through heating or freeze-drying creates the absorbent macroporous particles.

Other forms of absorbent macroporous particles 3 include what are generally referred to as aerogels. Aerogels are highly porous materials and typically have a much lower density than other absorbent materials. As used herein, the term "aerogel" includes any highly porous material prepared by removing the liquid from a gel, in such a way that an essentially dry absorbent macroporous structure of the gel material is retained.

It is believed that fluids are quickly drawn into absorbent macroporous materials, including aerogels, because of the high capillary attraction created by the large pores of these absorbents. These high capillary attraction forces are due to the fact that absorbent macroporous particles provide a combination of high capillary and osmotic force, with channels that are large enough to provide rapid fluid flow. These macropores, however, being small enough to retain the absorbed fluid, thereby avoiding "rewetting" of the absorbent article 1.

The term "aerogel" was coined by S. S. Kistler in U.S. Pat. No. 2,188,007, which is incorporated herein by reference. Kistler produced aerogels from a variety of compounds including cellulose, collodion, gelatin, albumin, alumina, nickel hydroxide, thoria, titania, stannic oxide, magnesium hydroxide, chromic oxide, pyroxylin and various compounds of iron, cobalt, zinc, cadmium, barium, manganese, vanadium and copper. Kistler's method involved forming an aqueous gel or jelly with a gel material, and then exchanging the water with a solvent, typically alcohol, and then exchanging the alcohol in the gel with ethyl ether. The ether containing gel was then submerged in the solvent, and then placed in a pressure vessel. It was then heated under pressure to above the critical point of the solvent. This step filled the gel with gas instead of liquid. The gaseous ether was then allowed to escape from the vessel while maintaining the conditions within the vessel above the critical temperature of the solvent. The result was an expanded but dried gel of low density. Aerogels produced according to this method typically have densities in the range of 0.03 to 0.3 g/cm$^3$.

Xerogels are a type of aerogel in which the liquid has been removed from the gel under supercritical conditions. Hrubesh of The Lawrence Livermore National Laboratory modified the basic technique for forming aerogels by using condensed silica, a base catalyst and supercritical fluid extraction to achieve silica aerogels having an ultra low density of about 0.005 g/cm$^3$ (See, Robert Pool Science, 247 (1990), at 807).

Others have produced aerogels by crosslinking polymeric gel materials, such as chitosan. For example, Japanese Patent Publication No. 61-133143, published Jun. 20, 1986, and U.S. Pat. No. 4,833,237 to Kawamura et al., incorporated herein by reference, both refer to crosslinked granular bodies derived from a low molecular weight chitosan crosslinked with diisocyanate.

Cryogels are another form of aerogel in which the liquid is removed from a frozen gel by sublimation. Cryogels being dried while frozen are macroporous due to the particles being pre-swollen prior to liquid removal. This greatly enhances the inter-particle diffusivity of liquids (see U.S. Pat. No. 5,573,994 to Kabra et al.).

Figure 2:
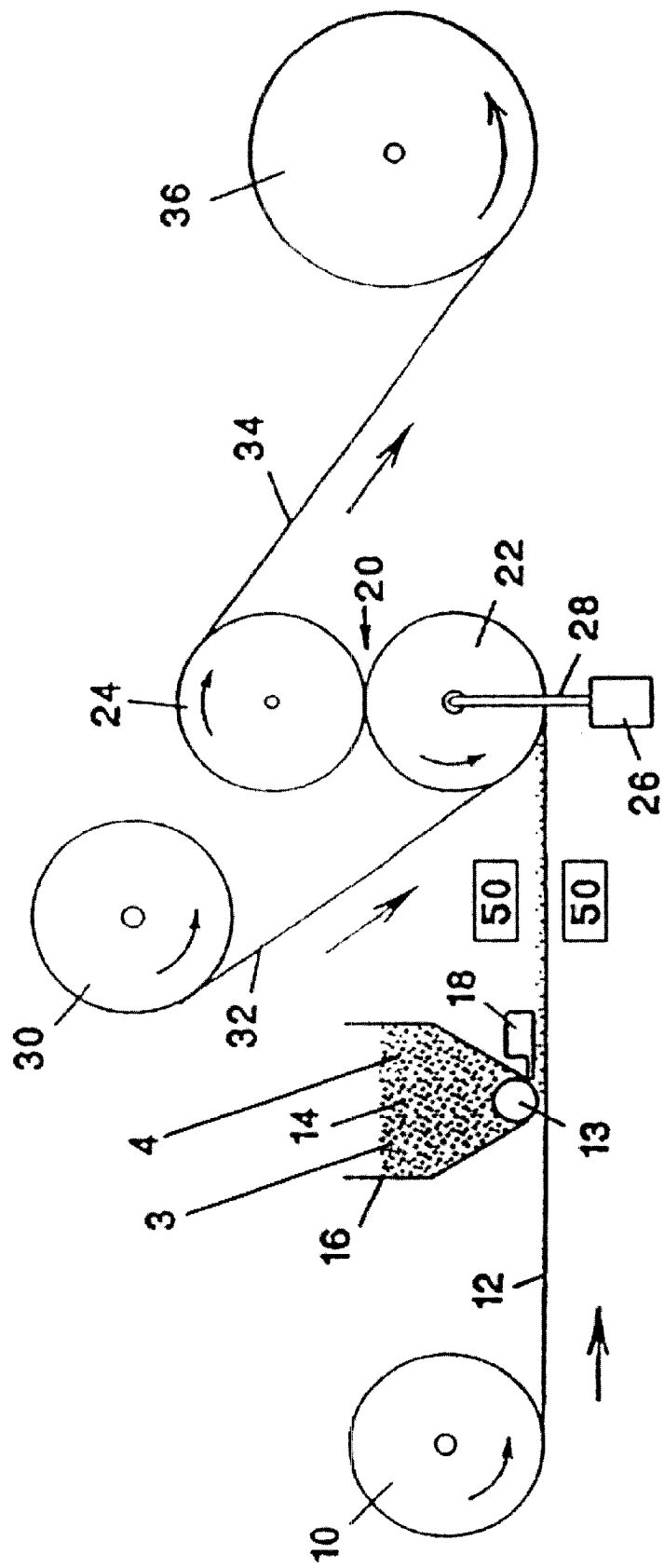
FIG. 2 is a schematic diagram illustrating an apparatus for the practice of the method of this invention.

FIG. 2 illustrates an exemplary apparatus used to produce this invention. A supply roll 10 provides a first substrate 12. Downstream from supply roll 10 is a knurled roller 13 positioned to receive a mixture of absorbent macroporous particles 3 and binder particles 4, generally indicated as mixture 14, from hopper 16. Mixture 14 is applied to the upper surface of substrate 12 as a continuous coating or, alternatively, as a coating in a specific design including, but not limited to, stripes.

Thereafter, substrate 12 containing mixture 14 is passed through nip 20 between a heated idler roller 22 and a drive roller 24. Alternatively, before being passed through nip 20, substrate 12 containing mixture 14, may be preheated by a pre-heater 50 such as, for example a convection or infrared oven. A pneumatic cylinder 26 is connected via a rod 28 to the axle of idler roller 22 to maintain a desired pressure on substrate 12 containing mixture 14 within nip 20. In passing through pre-heater 50, and over the surface of heated roller 22, mixture 14 is heated to a temperature equal to or greater than the softening temperature of binder particles 4, but to a temperature below the softening temperature of absorbent macroporous particles 3. Within nip 20, an amount of binder particles 4 coalesce under pressure with an amount of absorbent macroporous particles 3. An amount of binder particles 4 may also coalesce with first substrate 12.

Furthermore, in a preferred embodiment of the present invention, a second supply roll 30 of a second substrate 32, which may be of the same or may be of a different material from that of substrate 12, is also passed between nip 20 on the top of mixture 14. An amount of binder particles 4 may also coalesce with second substrate 32. Upon leaving nip 20, binder particles 4 cool and harden. The finished composite 34 then passes onto take-up roll 36.

By suitable selection of: substrate materials 12 and 32, binder particles 4, absorbent macroporous particles 3, absorbent macroporous particle 3 to binder particle 4 weight ratios, absolute amounts of mixture 14 applied to substrate 12 per unit area, binder particle 4 size, absorbent macroporous particle 3 size, the ratio of binder particle 4 size to absorbent macroporous particle 3 size, heating temperature, nip pressure and linear speed of first substrate 12, it is possible to vary the composite depth, average porosity, permeability, tensile strength, flexibility, pleatability, draping ability, wicking, absorption, adsorption, or other attributes of the absorbent macroporous composite of the present invention.

Although the absorbent article of the present invention has been described with respect to one or more particular embodiments, it will be understood that other embodiments of the present invention may be employed without departing from the spirit and scope of the present invention. Hence, the present invention is deemed limited only by the appended claims and the reasonable interpretation thereof.

What is claimed is:

1. An absorbent article comprising: a first substrate and a laminate, wherein said laminate comprises a mixture of binder particles and absorbent macroporous particles.

2. The absorbent article of claim 1, wherein said binder particles are on average smaller than said absorbent macroporous particles.

3. The absorbent article of claim 1, wherein at least some of said absorbent macroporous particles are coalesced by said binder particles to each other, to said first substrate, or to both each other and to said first substrate.

4. The absorbent article of claim 1, further comprising a second substrate on said laminate.

5. The absorbent article of claim 4, wherein at least some of said absorbent macroporous particles are coalesced by said binder particles to each other, to said first substrate, to said second substrate, or to any combinations thereof; and, said laminate is in-between said first substrate and said second substrate.

6. The absorbent article of claim 1, wherein said absorbent macroporous particles are selected from the group consisting of: aerogels, xerogels, cryogels, and a combination thereof.

7. The absorbent article of claim 1, wherein said absorbent macroporous particles have pores having a size from about 90 nm to about 1,000 nm across.

8. The absorbent article of claim 1, wherein said absorbent macroporous particles have a density from about 0.005 $g/cm^3$ to about 0.5 $g/cm^3$.

9. The absorbent article of claim 1, wherein said absorbent macroporous particles were produced by a process comprising the steps of: forming liquid-containing gel particles, and removing said liquid from said gel particles.

10. The absorbent article of claim 9, wherein said liquid-containing gel particles were formed from a gel material selected from the group consisting of: an alkoxysilane, metal oxide, alumina, biopolymer, organic polymer, silica, carbon and a combination thereof.

11. The absorbent article of claim 10, wherein said gel material is crosslinked.

12. The absorbent article of claim 1, wherein said absorbent macroporous particles have an average particle size from about 5 microns to about 5,000 microns.

13. The absorbent article of claim 1, wherein at least some of said binder particles are hydrophobic.

14. An absorbent article comprising:
a first substrate; and
a laminate comprising a mixture of binder particles and absorbent macroporous particles wherein said binder particles are on average about 4 to about 25 times smaller than said absorbent macroporous particles.

* * * * *